US00PP10639P

United States Patent [19]

Olesen et al.

[11] Patent Number: Plant 10,639

[45] Date of Patent: Oct. 13, 1998

[54] CLIMBING ROSE PLANT NAMED 'POULCLIMB'

[75] Inventors: Pernille Olesen; Mogens Olesen, both of Fredensborg, Denmark

[73] Assignee: Weeks Wholesale Rose Grower, Inc., Upland, Calif.

[21] Appl. No.: 961,530

[22] Filed: Oct. 30, 1997

[51] Int. Cl.[6] ..... A01H 5/00

[52] U.S. Cl. ..... Plt./2

[58] Field of Search ..... Plt./1, 2

*Primary Examiner*—Howard J. Locker

*Attorney, Agent, or Firm*—Christie, Parker & Hale, LLP

[57] ABSTRACT

A new plant variety of Climbing rose suitable for garden decoration, having flowers of irregularly striped deep pink and cream coloration.

1 Drawing Sheet

BACKGROUND OF THE INVENTION

This invention relates to a new and distinct variety of Climbing Rose. The varietal denomination of the new variety is 'Poulclimb'. It has as its seed parent the variety known as 'Poulvita' and an unnamed, undistributed seedling as its pollen parent.

SUMMARY OF THE INVENTION

Among the features which distinguish the new variety from other presently available and known commercial rose cultivars are the following combination of characteristics: its stems with very few prickles, its bright red styles, its irregular striping pattern from under to upper petal surfaces, and its large clusters of flowers. The plant is a large climbing plant, suitable for outdoor garden decoration.

Asexual reproduction of the new variety by budding as performed in Kern County and Upland, Calif., shows that the foregoing and other distinguishing characteristics come true to form and are established and transmitted through succeeding propagations. 'Poulclimb' may be asexually propagated by cuttings, budding, and grafting.

COMPARISON WITH PARENTS

The new rose may be distinguished from its seed parent, 'Poulvita', by the following combination of characteristics: whereas, 'Poulclimb' bears irregularly striped flowers of pink and cream coloration, 'Poulvita' bears flowers of an even cream coloration. The seed parent bears flowers of very double petalage, whereas the new rose bears flowers with significantly lower petalage (about 10 to 15). 'Poulclimb' is classified as a Climber with long canes, whereas 'Poulvita' is classified as a Floribunda with a compact significantly shorter plant habit.

The new variety may be distinguished from its pollen parent, by the following combination of characteristics: whereas the pollen parent bears irregularly striped flowers of a red and white coloration, 'Poulclimb' bears flowers irregularly striped with pink and cream. The new variety bears medium sized flowers of about 7.5 to about 9 cms. in diameter, whereas the pollen parent bears significantly smaller flowers of about 3 to 5 cms. in diameter. 'Poulclimb' is classified as a Climber with long canes, whereas the pollen parent is classified as a Miniature with significantly smaller plant habit.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon the Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in the month of September. Phenotypic expression may vary with environmental, cultural and climatic conditions, as well as differences in conditions of light and soil.

Flower

The new variety usually bears its flowers in clusters of five or more per stem. Flowers are borne in irregular rounded clusters on strong medium length stems (about 18 to about 30 cms.). Outdoors, the plant blooms very freely and nearly continuously during the growing season. The flowers have a moderate sweet apple-like fragrance. The lighter coloration in the petals is more evident in cooler temperatures. The pattern of striping on the under surfaces of the petals differs from the pattern of striping on the upper surfaces of the petals.

Bud

The peduncle is about 4 to about 5.5 cms. in length, of average caliper, and usually erect. It is moderately smooth, with some stipitate glands. Peduncle color is between 144A and 146C.

Before the calyx breaks, the bud is about 1.4 to about 1.8 cms. in diameter at the widest point, about 1.9 to about 2.4 cms. in length, and pointed to ovoid in shape.The surface of the bud bears every few stipitate glands and some fine hairs, usually with foliaceous parts extending beyond the tip of the bud equal to ¼ or less of its length. Bud color is between 144A and 146C.

The inner surface of the sepals is covered with fine wooly tomentum; sepal margins are lined with some stipitate glands and hairs.

As the petals open, the bud is about 1.6 to about 2 cms. in diameter at the widest point, about 2.2 to about 2.8 cms.

in length, and pointed to ovoid in form. The color of the under surfaces of the newly opened petals is irregularly striped and with flecks as dark as between 53D and 59D or as light as between 159D and 11D. At the point where the petal attaches, there is a moderately small zone of between 3C and 5C. The color of the upper surfaces of the newly opened petals is irregularly striped and with flecks as dark as between 53C and 60B or as light as between 159D and 11D. At the point where the petal attaches, there is a medium sized zone of between 3C and 5C.

Bloom

When fully open, the bloom ranges from about 7.5 to about 9 cms. in diameter. Petalage is semi-double with about 10 to 15 petals and about 1 to 3 petaloids arranged regularly. When partially open, the bloom form is somewhat high centered, and the shape of petals is moderately cupped. Petal edges somewhat roll outward. When fully open, the bloom form is more flat to cupped, and the petals are loosely cupped to undulated with petal edges only slightly rolled outward.

Petals

The substance of the petals is average and of medium thickness, with upper surfaces slightly satiny to velvety and under surfaces more shiny to satiny. The outer petals are nearly round to broadly obovate in shape with rounded apices. The inner petals are more narrowly obovate in shape with rounded apices.

Newly Opened Flower

The under surface of the outer, intermediate and inner petals is irregularly striped and with flecks as dark as between 54A and 61C or as light as between 159D and 11D. At the point where the petal attaches, there is a moderately small zone of between 3C and 5C. The upper surface of the outer, intermediate and inner petals is irregularly striped and with flecks as dark as between 58B and 60D or as light as between 159D and 11D. At the point where the petal attaches, there is a medium sized zone of between 3C and 5C.

The general tonality of the newly opened flower is irregularly striped and with flecks as dark as between 58B and 60D or as light as between 159D and 11D.

Three Day Old Flower

The under surface of the outer and inner petals is irregularly striped and with flecks as dark as between 63C and 58C or as light as between 155D and 65D. At the point where the petal attaches, there is a small zone of near 155D. The upper surface of the outer and inner petals is irregularly striped and with flecks as dark as between 64D and 68B or as light as between 155D and 65D. At the point where the petal attaches, there is a small zone of near 155D.

The general tonality of the three day old flower is irregularly striped and with flecks as dark as between 64D and 68D or as light as between 155D and 65D.

On the spent bloom, the petals usually drop off cleanly.

In September in Upland, Calif., blooms on the bush growing outdoors generaly last from about four to five or more days. Cut roses grown outdoors and kept at normal indoor living temperatures generally last from about four to five or more days.

Male Reproductive Organs

Stamens are average in number (approximately 80) and are arranged regularly about the pistil. The filaments are of irregular medium to long length, most with anthers. The anthers are moderately small for the class and all open approximately at the same time. Anther color is between 15A and 21C when immature and near 165A at maturity. Pollen is moderately abundant and near 16C in color.

Female Reproductive Organs

Pistils vary in number (approximately 35). The styles are somewhat uneven, of average to long length, average in caliper, and moderately bunched. Stigma color is near 2D. Style color is near 53A. Ovaries are usually all enclosed in the calyx.

Hips are of average length (about 1.7 to about 2 cms.), globular to nearly round in form, and near 25B in color when ripe. The hip surface is very smooth with moderately thick fleshy walls. There are approximately 14 to 20 seeds, medium in size.

Foliage

The compound leaves are usually comprised of three to seven leaflets and are borne abundantly. The leaves are about 9 to about 15 cms. in length and about 8.5 to about 11.5 cms. in width at the widest point, moderately heavy to leathery in texture, and somewhat glossy to semi-glossy in finish. The leaflets are about 4 to about 7.5 cms. in length and about 2.5 to about 4.5 cms. in width at the widest point, broadly oval in shape with acute apices and somewhat round bases. Their margins are usually serrate.

The upper surface of the mature leaf is between 137A and 137B. The under surface of the mature leaf is between 138B and 147B. The upper surface of the young leaf is between 146A and 144A, sometimes suffused with between 183C and 184A. The under surface of the young leaf is near 144A, sometimes lightly suffused with between 183C and 184A.

The rachis is average to heavy in caliper and very smooth. The upper side is shallowly grooved with very few hairs and stipitate glands on the edges of the grooves. The under side of the rachis is usually very smooth with few hairs and occasionally with a single small prickle.

The stipules are of medium length (about 1.3 to about 1.6 cms.) with moderately narrow somewhat short straight points that usually turn out at an angle of more than 45 degrees.

The plant displays an above average degree of resistance to powderly mildew, blackspot and rust as compared to other commercial varieties grown under comparable conditions in Upland, Calif.

Growth

The plant has a spreading climbing habit with long canes of about 300 to about 350 cms. in length. It displays very vigorous growth and the canes are of heavy caliper for the class.

The color of the major stem is near 146D. These are very few prickles. The prickles, when present, are about 0.7 to about 1 cm. in length, almost straight and angled moderately downward with a moderately short broad to rounded base; prickle color is near 166C.

The color of the branches is between 144A and 146A. Branches have very few prickles. The prickles, when present, are of similar size and shape to the prickles on the major stems; prickle color is near 160C.

The color of the new shoots is between 146A and 144A, sometimes suffused with between 183C and 184A. They are very few prickles. The prickles, when present, are of similar size and shape to the prickles on the major stems; prickle color is near 144A, often heavily suffused with between 183C and 184A.

We claim:

1. A new and distinct variety of Climbing rose plant substantially as described and illustrated herein.

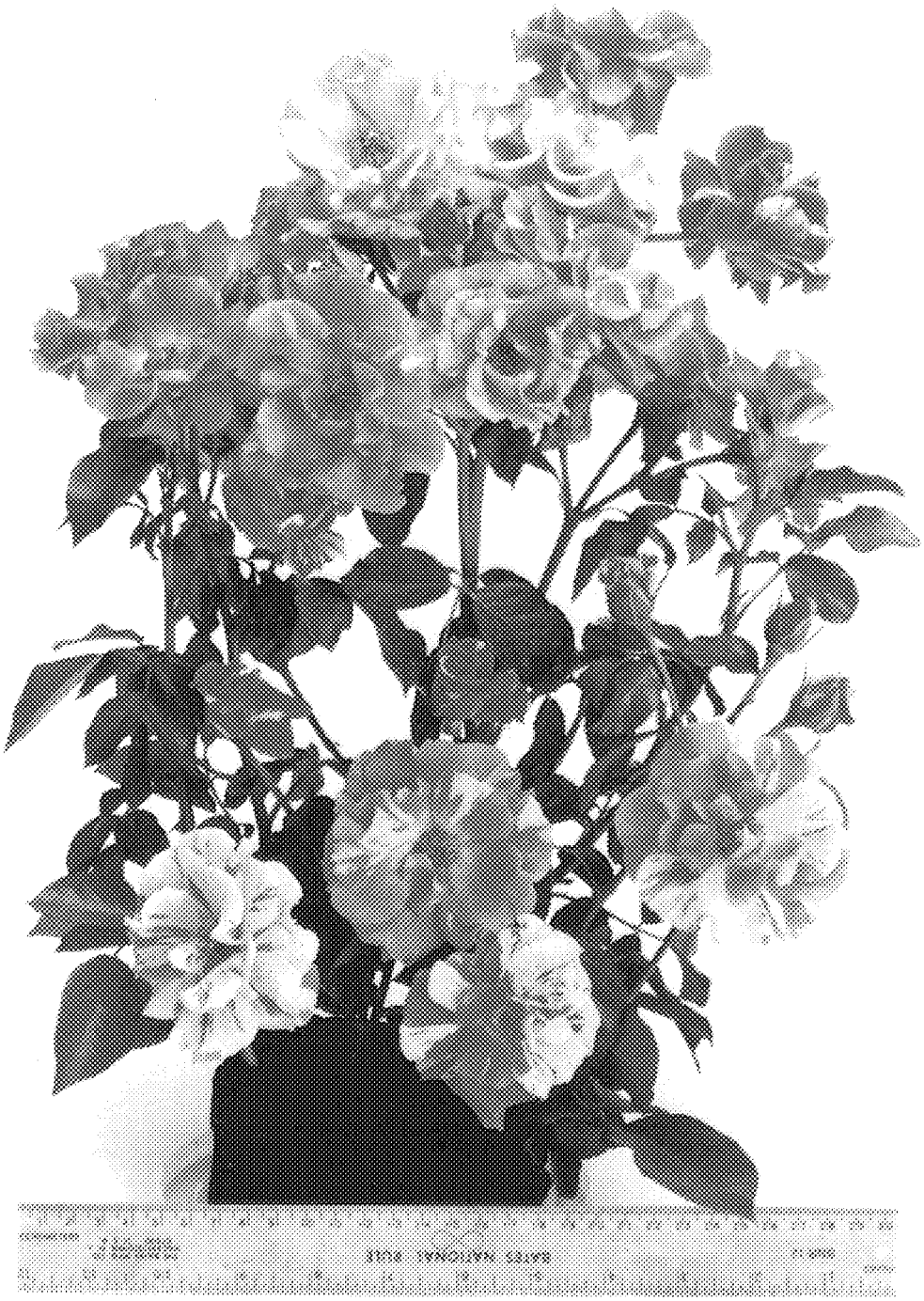

* * * * *